(12) United States Patent
Bonnefin et al.

(10) Patent No.: US 9,562,305 B2
(45) Date of Patent: Feb. 7, 2017

(54) YARN COMPRISING GEL-FORMING FILAMENTS OR FIBRES

(71) Applicant: CONVATEC TECHNOLOGIES INC., Las Vegas, NV (US)

(72) Inventors: Wayne Bonnefin, Clwyd (GB); Sarah Wroe, Clwyd (GB); Amelia Prentice, Clwyd (GB)

(73) Assignee: Convatec Technologies Inc., Las Vegas, NV (US)

( * ) Notice: Subject to any disclaimer, the term of this patent is extended or adjusted under 35 U.S.C. 154(b) by 0 days.

(21) Appl. No.: 14/362,050

(22) PCT Filed: Nov. 29, 2012

(86) PCT No.: PCT/GB2012/052952
§ 371 (c)(1),
(2) Date: May 30, 2014

(87) PCT Pub. No.: WO2013/079949
PCT Pub. Date: Jun. 6, 2013

(65) Prior Publication Data
US 2014/0305092 A1 Oct. 16, 2014

(30) Foreign Application Priority Data
Dec. 1, 2011 (GB) .................. 1120693.5

(51) Int. Cl.
*D02G 3/04* (2006.01)
*A61F 13/00* (2006.01)
(Continued)

(52) U.S. Cl.
CPC ........... *D02G 3/04* (2013.01); *A61F 13/00012* (2013.01); *A61F 13/00021* (2013.01);
(Continued)

(58) Field of Classification Search
CPC .................... A61F 13/00012; A61F 13/00021; A61F 13/00063; A61F 13/00068; A61F 13/0209; A61L 15/60; A61L 15/425; D06G 3/02; D06G 3/04; D06G 3/448; D06M 13/21; D06M 23/10; D04B 21/12; D01G 15/00; D01H 15/00; D06B 9/00
See application file for complete search history.

(56) References Cited

U.S. PATENT DOCUMENTS 4,984,570 A 1/1991 Langen et al.
5,731,083 A * 3/1998 Bahia et al. .................. 428/393
(Continued)

FOREIGN PATENT DOCUMENTS

CN 1307489 A 8/2001
EP 0525062 A1 2/1993
(Continued)

OTHER PUBLICATIONS

PCT-GB2012/052952 International Search Report issued Mar. 1, 2013.
(Continued)

*Primary Examiner* — Shaun R Hurley
(74) *Attorney, Agent, or Firm* — Wilson Sonsini Goodrich & Rosati

(57) ABSTRACT

A yarn comprising gel forming filaments or fibers particularly one used to make a woven or knitted wound dressing or other gelling fabric structure. The invention provides a yarn comprising a blend of from 30% to 100% by weight of gel-forming fibers and 0% to 70% by weight of textile fibers. Process for making the yarns are also described including those using rotor spinning.

17 Claims, 5 Drawing Sheets

| Yarn | CMC Content | Tex | Dry Tensile | | | | Wet Tensile | | | |
|---|---|---|---|---|---|---|---|---|---|---|
| | | | Breaking Strength (cN) | SD | Tenacity (cN / tex) | SD | Breaking Strength (cN) | SD | Tenacity (cN / tex) | SD |
| HF-2011/088 | 60% | 40.00 | 543.00 | 80.45 | 13.58 | 2.01 | 211.77 | 28.25 | 5.29 | 0.71 |
| HF-2011/108 | 70% | 40.00 | 556.13 | 66.28 | 13.90 | 1.66 | 152.48 | 27.25 | 3.81 | 0.68 |
| HF-2011/080 | 80% | 50.00 | 492.44 | 90.35 | 9.85 | 1.81 | 60.98 | 15.58 | 1.22 | 0.31 |

(51) Int. Cl.

| | | |
|---|---|---|
| *A61L 15/42* | (2006.01) | |
| *A61L 15/60* | (2006.01) | |
| *D02G 3/44* | (2006.01) | |
| *D06M 13/21* | (2006.01) | |
| *D06M 23/10* | (2006.01) | |
| *A61F 13/02* | (2006.01) | |
| *D04B 21/12* | (2006.01) | |
| *D01G 15/00* | (2006.01) | |
| *D01H 4/00* | (2006.01) | |
| *D02G 3/02* | (2006.01) | |
| *D06B 9/00* | (2006.01) | |
| *D06M 101/06* | (2006.01) | |

(52) U.S. Cl.
CPC .. *A61F 13/00063* (2013.01); *A61F 13/00068* (2013.01); *A61F 13/0209* (2013.01); *A61L 15/425* (2013.01); *A61L 15/60* (2013.01); *D01G 15/00* (2013.01); *D01H 4/00* (2013.01); *D02G 3/02* (2013.01); *D02G 3/448* (2013.01); *D04B 21/12* (2013.01); *D06B 9/00* (2013.01); *D06M 13/21* (2013.01); *D06M 23/10* (2013.01); *A61F 2013/0054* (2013.01); *A61F 2013/00174* (2013.01); *A61F 2013/00229* (2013.01); *A61F 2013/00242* (2013.01); *A61F 2013/00536* (2013.01); *D06M 2101/06* (2013.01); *D10B 2509/022* (2013.01); *Y10T 428/2975* (2015.01)

(56) References Cited

U.S. PATENT DOCUMENTS

| | | | |
|---|---|---|---|
| 6,268,544 B1 * | 7/2001 | Court et al. | 602/41 |
| 6,471,982 B1 * | 10/2002 | Lydon et al. | 424/443 |
| 6,548,730 B1 * | 4/2003 | Patel et al. | 602/56 |
| 6,656,496 B1 | 12/2003 | Kilpadi et al. | |
| 7,951,124 B2 | 5/2011 | Boehringer et al. | |
| 2002/0129596 A1 | 9/2002 | Driggars | |
| 2007/0066945 A1 | 3/2007 | Martin et al. | |
| 2007/0225663 A1 | 9/2007 | Watt et al. | |
| 2010/0042034 A1 | 2/2010 | Riesinger | |
| 2011/0282309 A1 | 11/2011 | Adie et al. | |
| 2012/0276183 A1 * | 11/2012 | Bradford | 424/409 |
| 2014/0323999 A1 * | 10/2014 | Bonnefin et al. | 604/319 |

FOREIGN PATENT DOCUMENTS

| | | | | |
|---|---|---|---|---|
| WO | WO-9116490 | | 10/1991 | |
| WO | WO 9312275 A1 * | | 6/1993 | A61L 15/28 |
| WO | WO-9312275 A1 | | 6/1993 | |
| WO | WO-95-19795 | | 7/1995 | |
| WO | WO-98-46818 | | 10/1998 | |
| WO | WO-9846818 A1 | | 10/1998 | |
| WO | WO-99-64080 | | 12/1999 | |
| WO | WO-00-01425 | | 1/2000 | |
| WO | WO-0001425 | | 1/2000 | |
| WO | WO-01-23653 | | 4/2001 | |
| WO | WO-2006052839 A2 | | 5/2006 | |
| WO | WO-2010085426 A1 | | 7/2010 | |
| WO | WO-2011-077096 | | 6/2011 | |
| WO | WO-2013079947 A1 | | 6/2013 | |
| WO | WO-2013079949 A1 | | 6/2013 | |

OTHER PUBLICATIONS

Chinese Patent Application No. 201280068502.7 Second Office Action dated Jun. 15, 2016.
Colombia Patent application No. 14-139575-8 Writ dated Jun. 1, 2016.
Australian Patent Application No. 2012343581 Examiners Second Report dated Jun. 27, 2016.
Australian Patent Application No. 2012343583 Patent Examination Report No. 1 dated Aug. 10, 2016.
Chinese Patent Application No. 201280068356.8 First Office Action issued on Jun. 8, 2015.
Chinese Patent Application No. 201280068356.8 Second Office Action issued on Apr. 18, 2016.
Chinese Patent Application No. 201280068502.7 First Office Action dated Sep. 6, 2015.
Columbia Patent Application No. 14-139580 Writ issued Jun. 1, 2016.
Karamuk et al., TISSUPOR: Development of a structured wound dressing based on a textile composite functionalized by embroidery technology. KTI Project No. 511, 2001. XP55054592. Available from: http//www.tissupor.com/pdf/tissuper_kti.pdf.
PCT Patent Application No. PCT/GB2012/052950 International Search Report dated Feb. 28, 2013.
PCT/GB2012/052950 International Preliminary Report on Patentability dated Jun. 3, 2014.
PCT/GB2012/052952 International Preliminary Report on Patentability issued Jun. 3, 2014.
U.S. Appl. No. 14/362,039 Restriction Requirement dated Aug. 10, 2016.
Colombian Patent Application No. 14-139575 Writ No. 11665 issued Oct. 19, 2016 (in Spanish) with foreign associate reporting letter dated Nov. 3, 2016 (in English).
New Zealand Patent Application No. 626695 Further Examination Report dated Sep. 9, 2016.
New Zealand Patent Application No. 723782 Examiner's First Report dated Sep. 9, 2016.
U.S. Appl. No. 14/362,039 Office Action dated Nov. 3, 2016.

* cited by examiner

| Yarn | CMC Content | Tex | Absorbency (g/g) | SD | Retention (g/g) | SD | Retention % | SD |
|---|---|---|---|---|---|---|---|---|
| HF-2011/088 | 60% | 40.00 | 6.35 | 0.51 | 3.87 | 0.25 | 61.04 | 1.68 |
| HF-2011/108 | 70% | 40.00 | 6.07 | 0.36 | 3.97 | 0.27 | 65.63 | 8.26 |
| HF-2011/080 | 80% | 50.00 | 7.03 | 0.09 | 5.66 | 0.26 | 80.54 | 3.87 |

FIG. 3.1

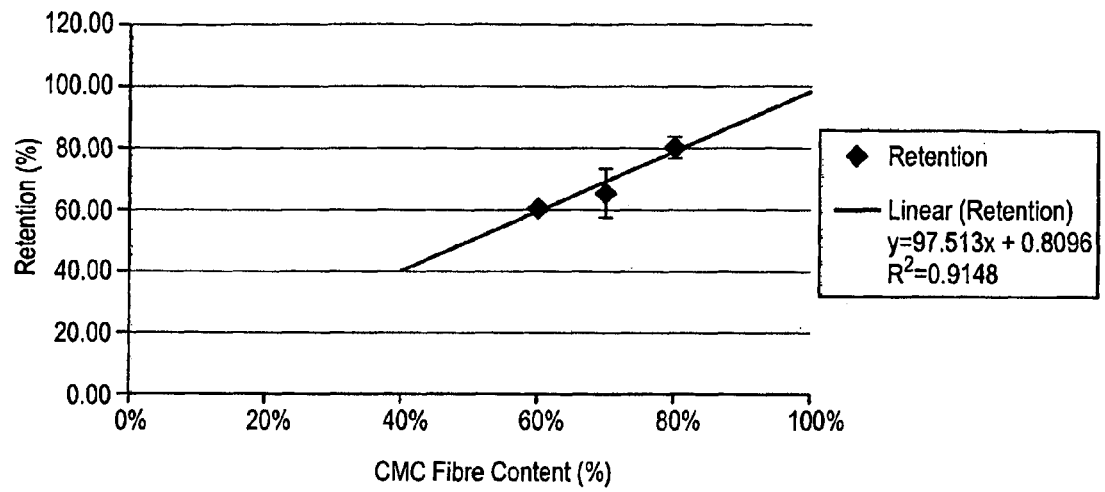
FIG. 3.2
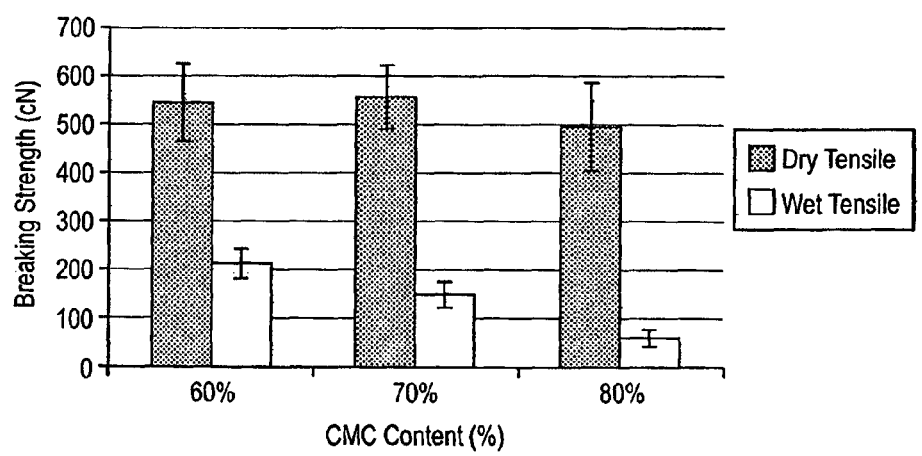
FIG. 3.3

| Yarn | CMC Content | Tex | Dry Tensile | | | | Wet Tensile | | | |
|---|---|---|---|---|---|---|---|---|---|---|
| | | | Breaking Strength (cN) | SD | Tanacity (cN / tex) | SD | Breaking Strength (cN) | SD | Tanacity (cN / tex) | SD |
| HF-2011/088 | 60% | 40.00 | 543.00 | 80.45 | 13.58 | 2.01 | 211.77 | 28.25 | 5.29 | 0.71 |
| HF-2011/108 | 70% | 40.00 | 556.13 | 66.28 | 13.90 | 1.66 | 152.48 | 27.25 | 3.81 | 0.68 |
| HF-2011/080 | 80% | 50.00 | 492.44 | 90.35 | 9.85 | 1.81 | 60.98 | 15.58 | 1.22 | 0.31 |

FIG. 4

| Yarn | Dry | Twist Angle α | Hydrated | Twist Angle α |
|---|---|---|---|---|
| HF-2011/088 | 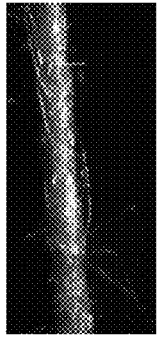 | 25.00° (2.11) | 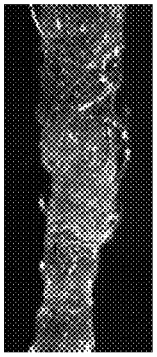 | 42.96° (6.10) |
| HF-2011/108 | 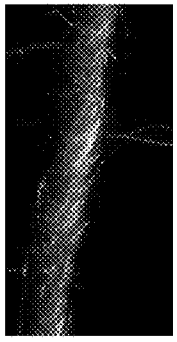 | 22.33° (3.57) |  | 37.99° (7.11) |
| HF-2011/080 | 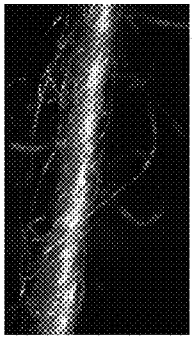 | 28.92° (3.33) | 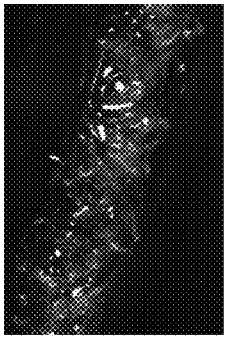 | 40.96° (2.85) |
FIG. 5

YARN COMPRISING GEL-FORMING FILAMENTS OR FIBRES

CROSS-REFERENCE

This application is a U.S. National Stage of PCT/GB2012/052952, filed Nov. 29, 2012; which claims the benefit of priority of GB1120693.5; filed Dec. 1, 2011; each of which is incorporated herein by reference in their entirety.

This invention relates to a yarn comprising gel-forming filaments or fibres and particularly one used to make a woven or knitted wound dressing or other gelling fabric structure.

It is known to make wound dressings from gel forming fibres. Typically such fibres are derived from a polysaccharide such as cellulose or alginate which is chemically modified in order to enhance the absorbency and gelling properties of the fibre.

Gel-forming fibres tend to be fragile and because of this their use has been confined to simple fabric structures such as those made using non woven techniques. For instance carding fibres into a non woven felt, layering the felts and needle punching to give a fabric with some integrity. This means that the variety of dressing types that can be made with staple gel forming fibres is restricted to those that can be made from non woven fabrics and thus their use is limited. For instance, it is difficult to prepare a wound dressing comprising gel forming fibres in a format that is to be subjected to tension as its non woven character means that it is weak in tension. It is also difficult to make certain shapes, for instance tubes or socks.

It would therefore be desirable to be able to make a yarn comprising gel-forming filaments or fibres, the yarn having sufficient strength that it can be processed into fabrics by weaving or knitting.

Accordingly the present invention provides a yarn comprising a blend of from 30% to 100% by weight of gel-forming fibres and 0% to 70% by weight of textile fibres.

Preferably the yarns comprise from 50% to 100% by weight of gel-forming fibres with the balance of textile fibres and most preferably from 60% to 100% by weight of gel-forming fibres with the balance of textile fibres.

By the term yarn is meant a thread or strand of continuous filament or staple fibres.

By gel forming filaments or fibres is meant hygroscopic filaments or fibres which upon the uptake of wound exudate become moist slippery or gelatinous and thus reduce the tendency for the surrounding fibres to adhere to the wound. The gel forming fibres can be of the type which retain their structural integrity on absorbtion of exudate or can be of the type which lose their fibrous form and become a structureless gel. The gel forming filaments or fibres are preferably spun sodium carboxymethylcellulose fibres or filaments, chemically modified cellulosic fibres or filaments, pectin fibres or filaments, alginate fibres or filaments, chitosan fibres or filaments, hyaluronic acid fibres or filaments, or other polysaccharide fibres or fibres or filaments derived from gums. The cellulosic fibres preferably have a degree of substitution of at least 0.05 carboxymethyl groups per glucose unit. The gel forming fibres or filaments preferably have an absorbency of at least 2 grams 0.9% saline solution per gram of fibre (as measured by the free swell absorbency method BS EN 13726-1:2002 Test methods for primary wound dressings—Part 1: Aspects of absorbency, Method 3.2 free swell absorptive capacity).

Preferably the gel forming fibres or filaments have an absorbency of at least 10 g/g as measured in the free swell absorbency method, more preferably between 15 g/g and 25 g/g.

The fibres present in the yarn preferably have a staple length of 30 to 60 mm, more preferably 40 to 55 mm and most preferably 45 to 55 mm.

Preferably the textile fibres or filaments have an absorbency of less than 10 g/g as measured by the free swell method and more preferably less than 5 g/g. Preferably the textile or filaments fibres are Tencel, cotton or viscose and may comprise lycra or other elastic fibre.

The yarns of the present invention preferably have a dry tensile strength of at least 10cN/tex, preferably from 10 to 40 cN/tex and most preferably from 16 to 35 cN/tex as measured by British Standard ISO 2062 2009.

A yarn made according to the processes of the present invention need not contain textile fibres enabling structures to be produced which consist wholly of gel-forming fibres.

The yarn of the invention can be made in various ways. The first is to spin gel-forming fibres to produce a spun gelling yarn. For example gel forming fibres which are for instance modified cellulose, or carboxymethyl cellulose or alginate can be spun into yarns comprising various blends of gel-forming staple fibres and textile fibres. The spinning may be done by first carding the fibres in the blend and spinning a yarn from the carded blend. The second is to chemically convert a cellulosic yarn to a gelling yarn either by starting with a spun cellulosic yarn or a filament cellulosic yarn.

We have found that particularly suitable yarns can be formed by rotor spinning or open end spinning. In such a process, staple gel-forming fibres are blended with textile fibres and carded to produce a continuous web. The web is condensed to produce a card sliver and then rotor spun. In rotor spinning, a high speed centrifuge is used to collect and twist individual fibres into a yarn. The yarns produced from this technique have the characteristics of a sufficient tensile strength to enable them to be further processed using knitting or weaving machinery.

A further embodiment of the invention provides a process for making a yarn comprising gel-forming fibres comprising the steps of:

blending staple gel-forming fibres optionally with textile fibres;

carding to form a continuous web;

drawing the web to produce a sliver and rotor spinning to produce a yarn.

The fibres present in the spun yarn preferably have a staple length of 30 to 60 mm, more preferably 40 to 55 mm and most preferably 45 to 55 mm.

A yarn made according to this process need not contain textile fibres enabling structures to be produced which consist of gel-forming fibres.

Alternatively a gelling yarn can be produced using a spun yarn consisting of natural cellulose fibres or solvent spun cellulose staple fibres or a blend of cellulose fibres and other textile fibres or by using a filament yarn of solvent spun cellulose which is then converted to chemically modify the yarns to produce gelling properties. For example, Lyocell yarns can be used as a starting material and converted in a kier process to impart gel-forming behaviour to the yarn.

A preferred method of converting the yarns or fabrics is described in WO 00/01425. For example the yarns or fabrics can be carboxymethylated by pumping a reaction fluid through the reaction vessel and therefore the cellulosic materials at 65° C. for 90 minutes. The reaction fluid is a solution of an alkali (typically sodium hydroxide) and sodium monochloroacetate in industrial denatured alcohol. After the reaction time, the reaction is neutralised with acid and washed before being dried in a laboratory oven for 1 hour at 40° C.

The invention is illustrated in the following drawings in which.

Figure 1:
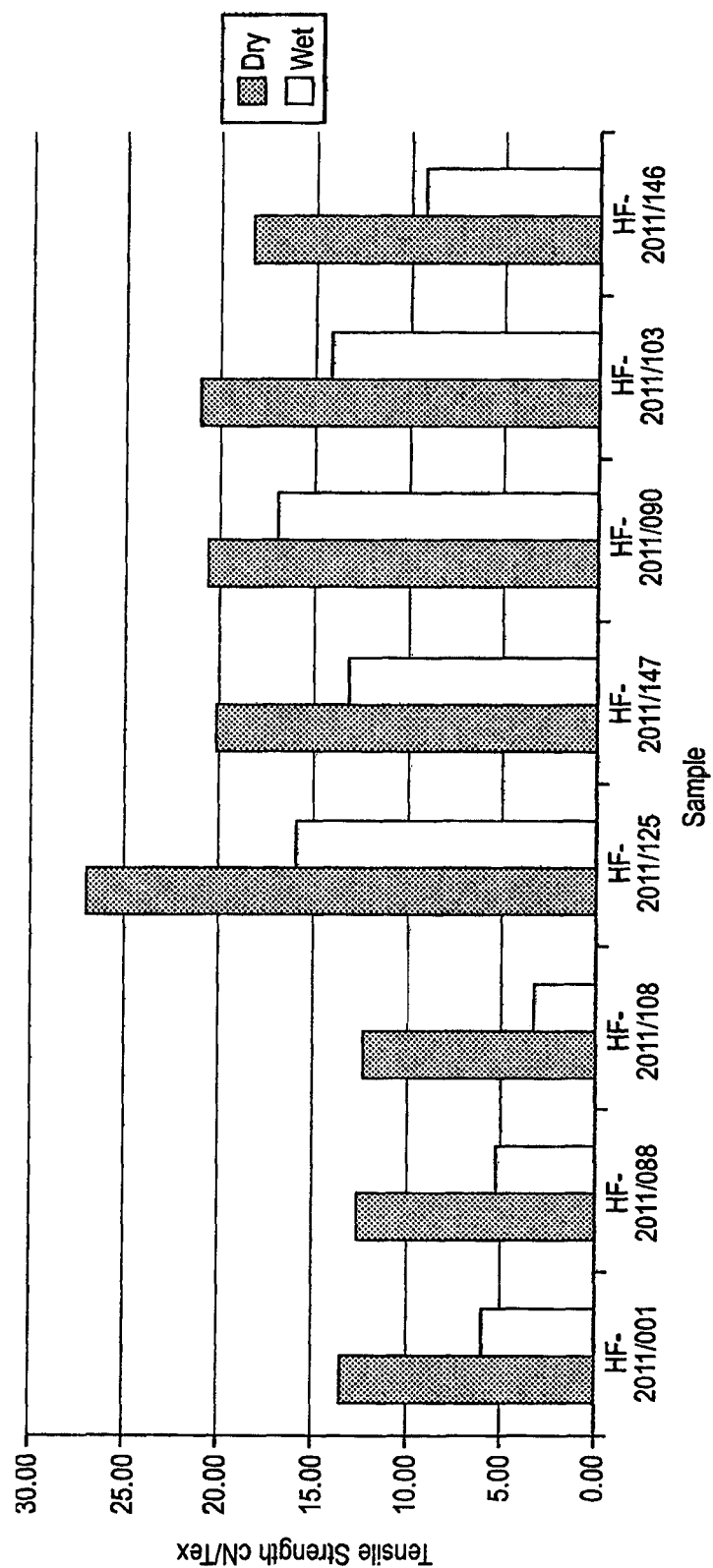
FIG. 1 shows a graph giving yarn tensile strength data for a number of yarns of the invention.

FIG. 3.1 shows a graph of fluid management against yarn fibre content for a number of yarns;

FIG. 3.2 shows a graph of fluid retention against yarn fibre content for a number of yarns;

FIG. 3.3 shows a graph of tensile strength against yarn fibre content for a number of yarns;

FIG. 4 shows Table 2 of Example 3 giving tensile strength data for a number of yarns of the invention; and FIG. 5 shows Table 3 which gives the helix angle and images of both dry and hydrated yarns for a number of yarns of the invention.

The invention will now be illustrated by the following examples.

EXAMPLE 1

Spinning Yarn from Staple Gel-Forming Fibres

Lyocell fibres and carboxymethyl cellulose staple fibres in blends of 50:50, 60:40 and 70:30 CMC:Lyocell were made by carding on a Trutzschler cotton card and spinning the resulting sliver at a twist of 650 turns/meter.

EXAMPLE 2

Converting a Textile Yarn to a Gel-Forming Yarn

Yarns were converted in the laboratory using a mini trier. In both trials, staple and filament lyocell yarns were converted. The yarns used for the conversion were staple $_{33}$ Tex Tencel®; HF-2011/090; and 20 Tex filament lyocell batches HF-2011/051 (trial 1) and HF-2011/125 (trial 2). Tencel® is a Lenzing owned, trademarked brand of lyocell and the Tencel® yarn used was a spun staple yarn. The filament lyocell was supplied by Acelon chemicals and Fiber Corporation (Taiwan) via Offtree Ltd.

The advantages of converting a yarn are that complete cones of yarn could potentially be converted in one relatively simple process, and the processing of gelling fibres is avoided, thus reducing the number of processing steps required and damage to the fibres.

Trial 1—Yarn Wrapped Around Kier Core

In this trial, Tencel® yarn was tightly wrapped around the perforated core of the kier using an electric drill to rotate the core and pull the yarn from the packages for speed. This meant that the yarn was wrapped tightly around the core under tension.

The yarn was converted by a process as described in WO 00/01425 in which carboxymethylation was carried out by pumping fluid through the kier and therefore the cellulosic materials at 65 C for 90 minutes. The reaction fluid was a solution of an alkali (typically sodium hydroxide) and sodium monochloroacetate in industrial denatured alcohol. After the reaction time, the reaction was neutralised with acid and washed before being dried in a laboratory oven for 1 hour at 40 C.

The conversion was successful and both staple and filament gelling yarns were produced; HF-2011/103 and HF-2011/105 respectively. Due to the tight and uneven wrapping of the staple yarn around the core, it had to be removed using a scalpel which left multiple short lengths (approximately 14 cm) of the converted yarn.

Trial 2—Small Yarn Hanks

The aim of the second trial was to produce longer lengths of converted yarns for testing hence a small hank was made of each the staple and filament lyocell yarns by hand and these were placed between layers of fabric for the conversion.

The yarn was converted by placing the hanks in a kier and converting to form a gel-forming fibre yarn as described above for Trial 1.

The conversion was successful and both staple and filament gelling yarns were produced; HF-2011/146 and HF-2011/147 respectively.

Yarn Summary

|  | Sample | HF# |
| --- | --- | --- |
| Gelling Yarns | 50:50 Spun staple gelling yarn | HF-2011/001 |
|  | 60:40 Spun staple gelling yarn | HF-2011/088 |
|  | 70:30 Spun staple gelling yarn | HF-2011/108 |
|  | Converted staple yarn (trial 1) | HF-2011/103 |
|  | Converted filament yarn (trial 1) | HF-2011/105 |
|  | Converted staple yarn (trial 2) | HF-2011/146 |
|  | Converted filament yarn (trial 2) | HF-2011/147 |
| Non-Gelling Yarns | Staple Tencel ® | HF-2011/090 |
|  | Filament lyocell (sample) | HF-2011/051 |
|  | Filament lyocell (bulk) | HF-2011/125 |

Results from Examples 1 and 2

With the exception of HF-2011/051, all of the yarns were tested for wet and dry tensile strength. Adaptations were made to the standard method BS EN ISO 2062:2009; "Textiles—Yarns from packages: Determination of single-end breaking force and elongation at break using constant rate of extension (CRE) tester". A Zwick tensile testing machine was used with a gauge length of 100 mm. The test uses a 100 N or 20 N liad cell to exert a constant rate of extension on the yarn until the breaking point is reached. Wet tensile testing was measured by wetting the samples with 0.2 ml of solution A in the central 3 to 4 cm of each yarn and leaving for 1 minute. The wetted sample was then placed in the jaws of the Zwick and clamped shut. Tensile strength was tested as the yarns produced need to be strong enough to withstand the tensions and forces applied during knitting, weaving and embroidery.

Tensile Strength

The results are shown in FIG. 1. All of the yarns were stronger when they were dry than when they were wet, with HF-2011/108, the 70:30 gelling yarn, showing the largest proportional strength decrease.

Of the yarns tested, HF-2011/108 was the weakest yarn both when wet and dry with tensile strengths of 12.4 and 3.4cN/Tex respectively, despite containing 30% lyocell fibres. Although this was the weakest yarn, it was successfully weft knitted; HF-2011/120 and woven; HF-2011/169 into fabrics, it is believed that all of the other yarns would also be strong enough to be converted into fabrics.

Both approaches successfully produced gelling yarns. For converted yarns, the spun and filament yarns behaved equivalently showing no advantage or disadvantage to having a twisted material in terms of fluid handling and strength of an 100% CMC yarn.

EXAMPLE 3

Yarns have been produced using open end spinning technology utilising 50 mm staple length CMC fibre. CMC has been blended with Tencel fibres in order to help the spinning process.

HF-2011/088—60%CMC 40% Tencel
HF-2011/108—70% CMC 30% Tencel
HF-2012/080—80% CMC 20% Tencel Fluid Handling The yarns were tested for their fluid handling capabilities using a modified version of TD-0187 'Liquid handling of dressings using direct immersion technique'. 3 m of yarn was used for each repeat and wrapped around a cylinder of 7.5 cm to give a constant number of twists. Samples were immersed in 10 ml of solution A for 30 minutes before being drained for 30 seconds and their hydrated weight measured. The amount of fluid retained was assessed by applying a vacuum to the sample for 1 minute and the final sample weight measured.

Tensile Strength

Tensile strength of the yarn was measured using the Zwick Universal Testing Machine (UTM). Samples were tested using a 20N load cell with a test speed of 100 mm/min and gauge of 100 mm. For wet strength, yarns were hydrated with 0.1 ml of solution A, prior to testing using the same machine settings.

Microscopy

Yarns were visually assessed using an optical microscope in a wet and dry state. The helix angle was also measured.

Results

Fluid Handling

Figure 2:
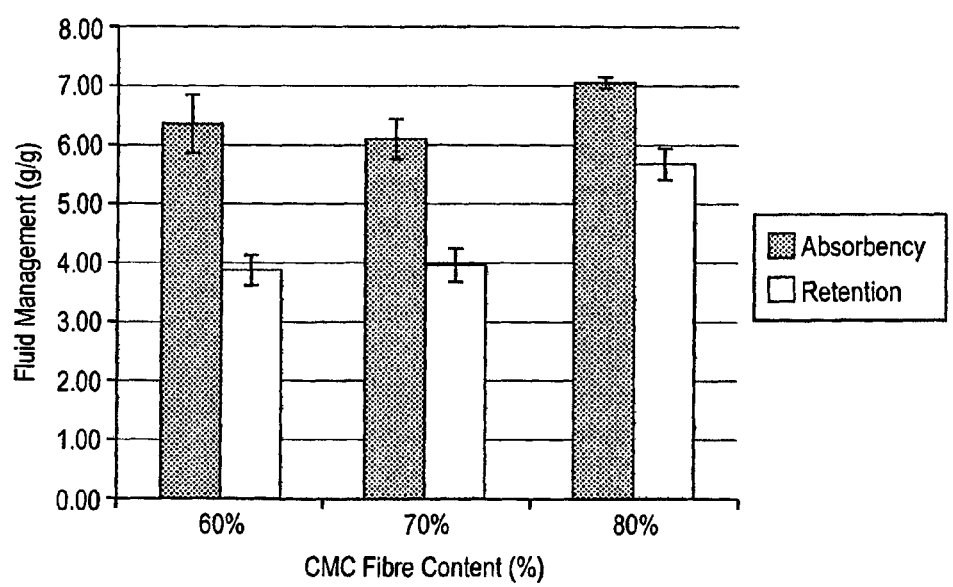
FIG. 2 shows Table 1 of Example 3 giving fluid handling data for a number of yarns of the invention.

An increased amount of CMC content caused an increase in the retention of the yarns, as shown in Table 1 (FIG. 2) and FIG. 3.1 and 3.2. There was a slight drop in absorbency when increasing the CMC content from 60% to 70% however the retention was improved.

In order to produce a fabric that has a comparative absorbency to Aquacel® of 0.18 g/cm$^{2(2)}$, theoretically a fabric of 256gsm should be formed from the 80% CMC yarn. In comparison Aquacel® has a weight per unit area of 119gsm[2].

Tensile Strength

Increased CMC content within the yarn also caused a decrease in the tensile strength shown in FIG. 3.3. However a satisfactory wet strength was still able to be achieved at 80% CMC content, with individual yarns providing more than double the strength of Aquacel® dressing per cm width in the machine direction (0.61N/strand of yarn in comparison to 0.21N/cm Aquacel®[2]), and almost equalling the dressing strength per cm width in the transverse direction (0.61N/strand of yarn in comparison to 0.66N/cm Aquacel®[2]). HF-2012/088 and HF-20122/108 have both been knitted successfully, and therefore the breaking strengths of these yarns are high enough to withstand tensions within the knitting process. HF-2012/108 was also woven using a leno structure; although some problems occurred suggesting a higher breaking strength is required for weaving. FIGS. 3.3 and 4 (Table 2) show the tensile strength data.

Microscopy

Visually the yarns gelled and swelled when hydrated. As the fibres swelled the helix angle of the twist increased, shown in Table 3 (FIG. 5), this is due to the increased yarn thickness. Some non gelling fibres are visible at this magnification.

Twist Factor

The twist factor of a yarn determines the yarn characteristics, and is dependent on the linear density of the yarn and the twist level. Since the twist angle, and properties resulting from this will vary depending upon the twist level and the yarn thickness the twist factor normalises yarns of different linear densities so that their twist properties can be compared. Table 4 outlines the twist factors used for cotton yarns for a number of end processes.

TABLE 4

Twist Factors most commonly used in cotton yarns[3]

| Yarn Application | Tex Count Twist Factor ($K_t$) |
| --- | --- |
| Soft Knitwear | 2400-2900 |
| Weft Yarn | 2900-3400 |
| Warp Yarn | 3900-4300 |
| Warp/Extra Strong Yarn | 5300-6300 |
| Crisp | 6800-8700 |

HF-2012/080 has a twist level of 580 turns/meter (given by the manufacturer). From this the twist factor can be calculated using the equation 7.

$$K_t = \sqrt{tex \times tpm} \qquad \text{(equation 7)}$$

Where
$K_t$ is the twist factor (using tex count)
Tex is the linear density of the yarn in tex
tpm is the twist level in turns per meter.
HF-2012/080–$K_t = \sqrt{50 \times 580} = 4101$.

This shows that the yarn is at its optimum twist for its strength.

The invention claimed is:

1. A yarn comprising a blend of from 30% to 100% by weight gel-forming fibres and 0% to 70% by weight textile fibres, wherein the fibres are rotor spun to produce the yarn, and the yarn has a dry tensile breaking strength of at least about 400 cN, the yarn capable of being converted into a fabric by knitting.

2. A yarn as claimed in claim 1 wherein the staple fibre length is from 30 to 60 mm.

3. A yarn as claimed in claim 1 having a dry tensile strength of at least 10cN/tex.

4. A yarn as claimed in claim 1 wherein the yarn comprises a blend of from 50% to 100% by weight of gel forming fibres with from 0% to 50% of textile fibres.

5. A process for making a yarn comprising gel-forming fibres comprising the steps of:
blending staple gel-forming fibres optionally with textile fibres;
carding to form a continuous web;
drawing the web to produce a sliver and rotor spinning to produce a yarn; wherein the yarn has a dry tensile breaking strength of at least about 400 cN.

6. A process for making a yarn comprising gel forming fibres or filaments, comprising the steps of
(i) obtaining a yarn of cellulosic filaments or fibres;
(ii) chemically modifying the yarn to give the yarn gel forming properties,
wherein the chemically modified yarn has a dry tensile strength of at least about 400 cN, the yarn capable of being converted into a fabric by knitting.

7. A process as claimed in claim 6 wherein the chemical modification is carboxymethylation using a reaction fluid comprising a solution of an alkali and monochloroacetate in an organic solvent.

8. A process for making a yarn as claimed in claim 5 wherein the tensile strength of the yarn is at least 10cN/tex.

9. A yarn as claimed in claim 1 wherein the gel forming fibres are polysaccharide fibres, chemically modified cellulosic fibres, pectin fibres, alginate fibres, chitosan fibres, hyaluronic acid fibres or fibres derived from gums.

10. A yarn as claimed in claim 1 wherein the gel forming fibres are modified cellulose fibres.

11. A process for making a yarn as claimed in claim 5 wherein the gel forming fibres are polysaccharide fibres, chemically modified cellulosic fibres, pectin fibres, alginate fibres, chitosan fibres, hyaluronic acid fibres or fibres derived from gums.

12. A process for making a yarn as claimed in claim 5 wherein the gel forming fibres are modified gel forming fibres.

13. A process for making a yarn as claimed in claim 6 wherein the tensile strength of the yarn is at least 10 cN/tex.

14. A process for making a yarn as claimed in claim 6, wherein the gel forming fibres are polysaccharide fibres, chemically modified cellulosic fibres, pectin fibres, alginate fibres, chitosan fibres, hyaluronic acid fibres or fibres derived from gums.

15. A process for making a yarn as claimed in claim 6 wherein the gel forming fibres are modified gel forming fibres.

16. A process for making a yarn as claimed in claim 5, wherein the gel forming fibres are modified cellulose fibres.

17. A process for making a yarn as claimed in claim 6, wherein the gel forming fibres are modified cellulose fibres.

* * * * *